(12) United States Patent
Boden et al.

(10) Patent No.: US 10,322,125 B2
(45) Date of Patent: Jun. 18, 2019

(54) TGF-BETA ENHANCING COMPOSITIONS FOR CARTILAGE REPAIR AND METHODS RELATED THERETO

(71) Applicants: EMORY UNIVERSITY, Atlanta, GA (US); THE UNITED STATES OF AMERICA REPRESENTED BY THE DEPARTMENT OF VETERANS AFFAIRS, Washington, DC (US)

(72) Inventors: Scott D Boden, Atlanta, GA (US); Sreedhara Sangadala, Dallas, GA (US)

(73) Assignees: Emory University, Atlanta, GA (US); The United States of America as represented by the Department of Veteran Affairs, Washington, DC (US)

( * ) Notice: Subject to any disclaimer, the term of this patent is extended or adjusted under 35 U.S.C. 154(b) by 0 days.

(21) Appl. No.: 14/768,563

(22) PCT Filed: Feb. 18, 2014

(86) PCT No.: PCT/US2014/016771
§ 371 (c)(1),
(2) Date: Aug. 18, 2015

(87) PCT Pub. No.: WO2014/130411
PCT Pub. Date: Aug. 28, 2014

(65) Prior Publication Data
US 2015/0374694 A1    Dec. 31, 2015

Related U.S. Application Data

(60) Provisional application No. 61/767,867, filed on Feb. 22, 2013.

(51) Int. Cl.
| A61K 31/15 | (2006.01) |
| A61K 31/357 | (2006.01) |
| A61K 31/517 | (2006.01) |
| A61K 31/404 | (2006.01) |
| A61K 31/47 | (2006.01) |
| A61K 31/4706 | (2006.01) |
| A61K 31/505 | (2006.01) |

(52) U.S. Cl.
CPC ............ *A61K 31/517* (2013.01); *A61K 31/15* (2013.01); *A61K 31/357* (2013.01); *A61K 31/404* (2013.01); *A61K 31/47* (2013.01); *A61K 31/4706* (2013.01); *A61K 31/505* (2013.01)

(58) Field of Classification Search
CPC .............................. A61K 31/15; A61K 31/357
See application file for complete search history.

(56) References Cited

U.S. PATENT DOCUMENTS

| 5,147,854 A | 9/1992 | Newman | |
| 5,595,722 A * | 1/1997 | Grainger | A61K 9/0024 424/9.2 |
| 7,713,987 B2 * | 5/2010 | Bhamidipati | C07D 498/04 514/224.2 |
| 2003/0175257 A1 | 9/2003 | Song | |
| 2005/0245540 A1 * | 11/2005 | Takeshita | A61K 31/496 514/254.09 |
| 2006/0276433 A1 * | 12/2006 | Kawagoe | A61K 31/15 514/63 |

FOREIGN PATENT DOCUMENTS

| WO | 1998051317 | 11/1998 |
| WO | WO 2006/029850 A1 * | 3/2006 |
| WO | 2008021795 | 2/2008 |
| WO | WO 2010/033507 A1 * | 3/2010 |

OTHER PUBLICATIONS

Bansal et al. Med. Chem. Res., 2011, vol. 20, pp. 1482-1489.*
Zhang et al. Bioorganic & Medicinal Chemistry, 2009, vol. 17, pp. 2077-2090.*
Okano et al. Bioorganic & Medicinal Chemistry, 2009, vol. 17, pp. 119-132.*
Yilmaz et al. Journal of Enzyme Inhibition and Medicinal Chemistry, 2012, vol. 27, No. 3, pp. 428-436.*
Shirinzadeh et al. Z. Naturforsch, 2011, vol. 66c, pp. 340-344.*
MUFTIC (Quarterly Journal of Crude Drug Research, 1969, vol. 9, No. 4, pp. 1455-1459) (Year: 1969).*
Ballock et al., The regulation of the expression of the type-II collagen gene by members of the TGF-β superfamily. See J Orthop Res, 1997, 15:463-467.
Beuningen et al. Protection from interleukin 1 induced destruction of articular cartilage by TGF-β . See Ann Rheum Dis, 1993, 52:185-191.
Davidson et al. Reduced TGF-β signaling in cartilage has a role in impaired repair capacity. Arthritis Research & Therapy, 2007, 7(6):R1338.
Man et al. Protection of articular cartilage from degeneration by injection of transforming growth factor-beta in temporomandibular joint osteoarthritis', Oral Surgery, Oral Medicine, Oral Pathology, Oral Radiology, and Endodontology, 2009, vol. 108, pp. 335-340.
Wang et al. Recent progress in understanding molecular mechanisms of cartilage degeneration during osteoarthritis, Ann. N.Y. Acad. Sci. 1240 (2011) 61-69.

* cited by examiner

*Primary Examiner* — James D. Anderson
(74) *Attorney, Agent, or Firm* — Emory Patent Group

(57) ABSTRACT

This disclosure relates to compounds and compositions for cartilage repair and methods related thereto. In certain embodiments, the disclosure relates to methods of inducing cartilage growth and regeneration comprising administering an effective amount of a composition comprising a compound disclosed herein to the subject or implanting a cartilage matrix comprising a compound disclosed herein in the subject. In certain embodiments, the compound is used locally such as injection at any desired site of cartilage formation.

27 Claims, 6 Drawing Sheets

Specification includes a Sequence Listing.

TGF-BETA ENHANCING COMPOSITIONS FOR CARTILAGE REPAIR AND METHODS RELATED THERETO

CROSS REFERENCE TO RELATED APPLICATIONS

This Application claims priority to U.S. Provisional Application No. 61/767,867 filed Feb. 22, 2013, hereby incorporated by reference in its entirety.

BACKGROUND

Osteoarthritis is common in the aging population and results in cartilage degeneration. See Wang et al., Ann. N.Y. Acad. Sci., 2011, 1240 61-69. Characteristic features of osteoarthritis include changes in articular cartilage, chondrocyte hypertrophy, and increased remodeling of the periarticular bone. Acetaminophen is the first line treatment for osteoarthritis followed by non-steroidal anti-inflammatory drugs for mild to moderate symptoms. If disability is significant and anti-inflammatory drugs are ineffective, joint replacement surgery is typical. There is currently no effective disease-modifying treatment for osteoarthritis. Thus, there is a need to identify improved therapies.

Articular cartilage damage is an important pathologic feature leading to joint dysfunction. Articular cartilage is a reversibly compressible tissue that protects the underlying bones from biomechanical damage and is comprised mostly of collagen. The non-collagenous matrix is made up of proteoglycans. Chondrocytic cells are embedded in the matrix networks. They produce and maintain the cartilage by synthesizing and degrading matrix components. Mesenchymal precursor cells are involved with the development of mature articular cartilage and differentiate into chondrocytes.

Transforming growth factor beta (TGF-β) is a secreted protein that exists in different isoforms, e.g., TGF-β1, TGF-β2 and TGF-β3. TGF-β proteins effect cellular proliferation and differentiation. The TGF-β family is part of a superfamily of proteins known as the transforming growth factor beta superfamily which includes bone morphogenetic proteins. Davidson et al. report that reduced TGF-β signaling in cartilage has a role in impaired repair capacity. See Arthritis Research & Therapy, 2007, 7(6):R1338. Ballock et al., report the regulation of the expression of the type-II collagen gene by members of the TGF-β superfamily. See J Orthop Res, 1997, 15:463-467. Beuningen et al. report protection from interleukin 1 induced destruction of articular cartilage by TGF-β. See Ann Rheum Dis, 1993, 52:185-191.

SUMMARY

This disclosure relates to compounds and compositions for cartilage repair and methods related thereto. In certain embodiments, the disclosure relates to methods of inducing cartilage growth and regeneration comprising administering an effective amount of a composition comprising a compound disclosed herein to the subject or implanting a cartilage matrix comprising a compound disclosed herein in the subject. In certain embodiments, the compound is used locally such as injection at any desired site of cartilage formation. In certain embodiments, the composition is administered by injection of a syringe or catheter comprising a lumen for injecting the composition slid through an incision about the area of damaged cartilage.

In certain embodiments, the disclosure relates to pharmaceutical compositions comprising a TGF-β enhancing compound or salt thereof and a pharmaceutically acceptable excipient. In certain embodiments, the compound is 1-ethylidene-2-phenylhydrazine, pyrimidine-2,4-diamine, 3-benzylideneindolin-2-one, quinolin-4-amine, quinazolin-4-amine, derivatives, or salts thereof. In certain embodiments, the derivative is a compound disclosed herein optionally comprising one or more, the same or different, substituents or salts thereof.

In certain embodiments, the pharmaceutical composition is formulated to release over a 12 hour, 1 day, 3 day, 5 day, 7 day, two week, or one month period. In certain embodiments, the administration is localized. In certain embodiments, administration is achieved through oral delivery, intravenous delivery, parenteral delivery, intradermal delivery, percutaneous delivery, or subcutaneous delivery.

In certain embodiments, the disclosure relates to methods of treating or preventing damaged cartilage from physical injury or chondrodystrophies comprising administering an effective amount of a compound disclosed herein to a subject in need thereof. In certain embodiments, the subject is diagnosed with, exhibiting symptoms of, or at risk of osteoarthritis, achondroplasia, costochondritis, spinal disc herniation, or polychondritis.

In certain embodiments, the compound is administered or implanted in combination with progenitor cells, autologous mesenchymal stem cells, autologous peripheral blood progenitor cells, autologous chondrocytic cells, a TGF-β protein, hyaluronic acid, proteoglycans, growth factors or combinations thereof.

In certain embodiments, methods of treating or preventing damaged cartilage from physical injury or chondrodystrophies comprises creating lesions surgically in the cartilage of a subject extending into subchondral bone and administering a compound disclosed herein in the subject in the area of created lesions.

In certain embodiments, the disclosure relates to methods of treating or preventing damaged cartilage from physical injury or chondrodystrophies comprising creating lesions surgically in the cartilage of a subject extending into subchondral bone and implanting a cartilage matrix comprising a compound disclosed herein to the subject in the area of created lesions.

In certain embodiments, the disclosure relates to methods of treating or preventing damaged cartilage from physical injury or chondrodystrophies comprising creating lesions surgically in the cartilage of a subject extending into subchondral bone and implanting a cartilage matrix in the area of created lesions, and administering a compound disclosed herein to the subject in the area of created lesions. In certain embodiments, the cartilage matrix comprises collagen or polymer. In certain embodiments, the cartilage matrix comprises progenitor cells, autologous mesenchymal stem cells, autologous peripheral blood progenitor cells, autologous chondrocytic cells, a TGF-β protein, hyaluronic acid, proteoglycans, growth factors, or combinations thereof. In certain embodiments, the method further comprises the step of administering progenitor cells, autologous mesenchymal stem cells, autologous peripheral blood progenitor cells, autologous chondrocytic cells, a TGF-β protein, hyaluronic acid, proteoglycans, growth factors, or combinations thereof in the area of created lesions.

In certain embodiments, the disclosure relates to a cartilage matrix comprising a compound disclosed herein or salt thereof. Typically the cartilage matrix comprises collagen or a polymer. Optionally the matrix further comprises progenitor cells, autologous mesenchymal stem cells (MSCs), autologous peripheral blood progenitor cells, autologous chondrocytic cells, a TGF-β protein, hyaluronic acid, proteoglycans, growth factors, or combinations thereof.

In certain embodiments, the disclosure relates to kits comprising a cartilage matrix and a compound disclosed herein or salt thereof. Optionally the kit further comprises progenitor cells, mesenchymal stem cells (MSCs), peripheral blood progenitor cells, chondrocytic cells, a TGF-β protein, hyaluronic acid, proteoglycans, growth factors, or combinations thereof. In certain embodiments, the kits further comprise a transfer device, such as a syringe, catheter, or pipette.

Compositions comprising a compound disclosed herein may be dripped into the matrix, optionally in combination with other components such as proteoglycans, isolated chondrocytic cells, mesenchymal stem cell, a TGF-β protein or other components disclosed herein.

In certain embodiments, the disclosure contemplates methods of implanting a cartilage matrix such as a collagen matrix comprising a compound disclosed herein in a subject at a site of desired collagen growth or regeneration. The compound could be used by itself with or without exogenous TGF-β or other growth factors.

In certain embodiments, the disclosure relates to methods of forming cartilage comprising implanting a collagen matrix optionally comprising a compound and optionally comprising a TGF-β protein and/or another growth factor in a subject at a site of cartilage growth and administering a pharmaceutical composition comprising a compound disclosed herein to the subject.

In certain embodiments, the disclosure relates to uses of compounds disclosed herein and derivatives or salts thereof for cartilage regeneration e.g., between intervertebral disc and articular, jaw, elbow, knee, ankle, wrist, and hip joints. Methods contemplate oral administration, intravenous administration, or direct injection at the desired site(s) of the subject.

In some embodiments, the disclosure relates to a cartilage matrix comprising a compound disclosed herein, derivatives, or salts thereof that are covalently linked or non-specifically absorbed to the matrix.

In some embodiments, the disclosure relates to a process for engineering cartilage tissue comprising combining a compound disclosed herein with a cell selected from the group consisting of pluripotent stem cells, mesenchymal cells, and embryonic stem cells.

Within certain embodiments, it is also contemplated that one or more of these compounds disclosed herein may be used alone or in combination with multiple compounds, with or without exogenous growth factors, and/or in combination with other agonists and promoting agents of the TGF-β pathway.

DETAILED DISCUSSION

Figure 1:
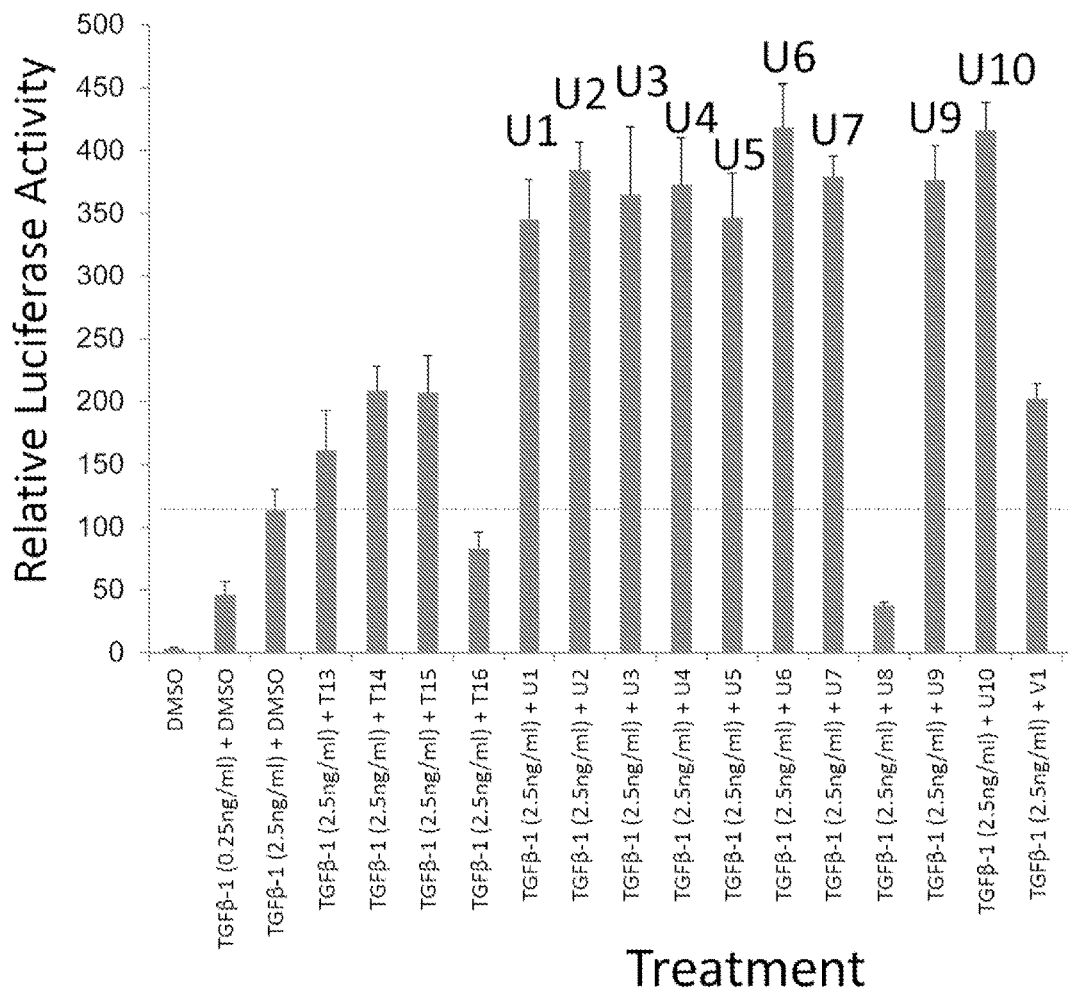
FIG. 1 shows activity data for tested compounds. U1 is 1-((6-chlorobenzo[d][1,3]dioxol-5-yl)methylene)-2-(3-chlorophenyl)hydrazine; U2 is 3-((2-(3-chlorophenyl)hydrazono)methyl)benzonitrile; U3 is 5-((2-(3-chlorophenyl)hydrazono)methyl)-2-methoxyphenol; U4 is 1-(2-chloro-6-fluorobenzylidene)-2-(3-chlorophenyl)hydrazine; U5 is 1-(3-chlorophenyl)-2-(3-methylbenzylidene)hydrazine; U6 is methyl 4-((2-(3-chlorophenyl)hydrazono)methyl)benzoate; U7 is 1-(3-chlorophenyl)-2-(2,4,6-trimethoxybenzylidene)hydrazine; U8 is 1-(3-chlorophenyl)-2-(2,4-dimethoxybenzylidene)hydrazine; and U9 is 3-((2-(3-chlorophenyl)hydrazono)methyl)-1H-indole

It had been discovered that a number of compounds are transforming growth factor beta (TGF-β) enhancers. TGF-β proteins effect cellular proliferation and differentiation. In certain embodiments, the disclosure relates to methods of inducing cartilage growth and regeneration comprising administering an effective amount of a composition comprising a compound disclosed herein to the subject or implanting a cartilage growth matrix comprising a compound disclosed herein in the subject. In certain embodiments, the compound is used locally such as injection at any desired site of cartilage formation. In certain embodiments, the composition is administered by injection of a syringe or catheter comprising a lumen for injecting the composition slid through an incision about the area of damaged cartilage.

Terms

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxy group. Contemplated derivative include switching carbocyclic, aromatic or phenyl rings with heterocyclic rings or switching heterocyclic rings with carbocyclic, aromatic or phenyl rings, typically of the same ring size. The derivative may be a prodrug such as esters of carboxylic acids. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, all hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

When used in reference to compound(s) disclosed herein, "salts" refer to derivatives of the disclosed compound(s) where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butyryl, 2-butyryl, 1-pentynyl, 2-pentynyl, 3-methyl-1-butyryl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulphur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" or "heteroaromatic" refers an aromatic heterocarbocycle having 1 to 4 heteroatoms selected from nitrogen, oxygen and sulphur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulphur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulphur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—CH$_3$).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfamoyl" refers to an alkyl as defined above attached through a sulfamoyl bridge (i.e., —S(=O)$_2$NHalkyl), and an "Arylsulfamoyl" refers to an alkyl attached through a sulfamoyl bridge (i.e., —S(=O)$_2$NHaryl).

"Alkylsulfinyl" refers to an alkyl as defined above with the indicated number of carbon atoms attached through a sulfinyl bridge (i.e. —S(=O)alkyl).

The terms "halogen" and "halo" refer to fluorine, chlorine, bromine, and iodine.

Compounds

Compounds and derivatives disclosed herein may be used for cartilage growth and related applications. Derivatives of certain compounds are further exemplified below. In certain embodiments, the compound is 1-ethylidene-2-phenylhydrazine, pyrimidine-2,4-diamine, 3-benzylideneindolin-2-one, quinolin-4-amine, quinazolin-4-amine, derivatives, or salts thereof.

In certain embodiments, the 1-ethylidene-2-phenylhydrazine derivative has the following formula:

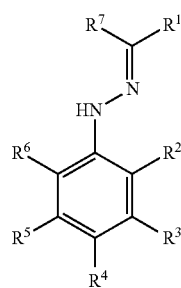

Formula I or salts thereof wherein $R^1$ is carbocyclyl, aryl, or heterocyclyl, wherein $R^1$ is optionally substituted with one or more, the same or different, $R^7$;

$R^2$, $R^3$, $R^4$, $R^5$, and $R^6$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^2$, $R^3$, $R^4$, $R^5$, and $R^6$ are optionally substituted with one or more, the same or different, $R^7$;

$R^7$ is hydrogen or alkyl, wherein $R^7$ is optionally substituted with one or more, the same or different, $R^8$; and $R^8$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is phenyl or heterocyclyl such as indolyl.

In certain embodiments, $R^7$ is hydrogen.

In certain embodiments, a compound of formula I is:

1-((6-chlorobenzo[d][1,3]dioxol-5-yl)methylene)-2-(3-chlorophenyl)hydrazine;
3-((2-(3-chlorophenyl)hydrazono)methyl)benzonitrile;
5-((2-(3-chlorophenyl)hydrazono)methyl)-2-methoxyphenol;
1-(2-chloro-6-fluorobenzylidene)-2-(3-chlorophenyl)hydrazine;
1-(3-chlorophenyl)-2-(3-methylbenzylidene)hydrazine;
methyl 4-((2-(3-chlorophenyl)hydrazono)methyl)benzoate;
1-(3-chlorophenyl)-2-(2,4,6-trimethoxybenzylidene)hydrazine;
1-(3-chlorophenyl)-2-(2,4-dimethoxybenzylidene)hydrazine; or
3-((2-(3-chlorophenyl)hydrazono)methyl)-1H-indole or salts thereof.

In certain embodiments, the pyrimidine-2,4-diamine derivative is a compound of following formula II:

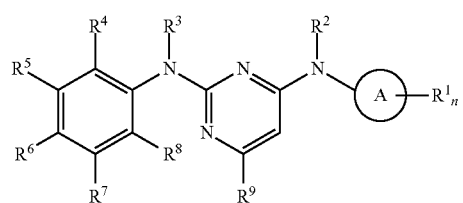

Formula II or salts thereof wherein,

A is a carbocyclyl, aryl, or heterocyclyl;

$R^1$ is at each occurrence, the same or different, hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$ is optionally substituted with one or more, the same or different, $R^{10}$;

n is 0, 1, 2, 3, 4, or 5;

$R^2$, $R^3$, $R^4$, $R^5$, $R^6$, $R^7$, $R^8$, and $R^9$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl) 2amino, alkylsulfinyl, alkylsulfonyl, arylsulfonyl, carbocyclyl, aryl, or heterocyclyl, wherein each $R^2$, $R^3$, $R^4$, $R^5$, $R^6$, $R^7$, $R^8$, and $R^9$ are optionally substituted with one or more, the same or different, $R^{10}$;

$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

$N^2$-(4-chlorophenyl)-$N^4$-(4-fluorophenyl)pyrimidine-2,4-diamine;
$N^2$-(2-fluoro-4-iodophenyl)-$N^4$-(4-fluorophenyl)pyrimidine-2,4-diamine; or
$N^2$-(3-chloro-4-methoxyphenyl)-$N^4$-cyclopropylpyrimidine-2,4-diamine or salts thereof.

In certain embodiments, the 3-benzylideneindolin-2-one derivative is a compound of formula III,

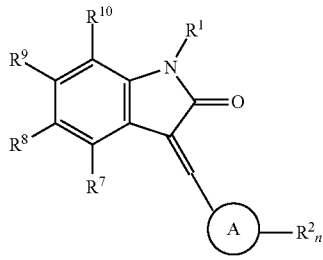

Formula III or salts thereof, wherein

A is a carbocyclyl, aryl, or heterocyclyl;

$R^1$, $R^7$, $R^8$, $R^9$, and $R^{10}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^7$, $R^8$, $R^9$, and $R^{10}$ are optionally substituted with one or more, the same or different, $R^{11}$;

$R^2$ is at each occurrence, the same or different, hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^2$ is optionally substituted with one or more, the same or different, $R^{11}$;

n is 0, 1, 2, 3, 4, or 5;

$R^{11}$ is alkyl, halogen, nitro, cyano, hydroxy, amino, mercapto, formyl, carboxy, alkanoyl, carbamoyl, alkoxy, alkylthio, alkylamino, (alkyl)2amino, alkylsulfinyl, alkylsulfonyl, arylsulfonyl, carbocyclyl, aryl, or heterocyclyl, wherein $R^{11}$ is optionally substituted with one or more, the same or different, R1$^2$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the 3-(benzylidene)indolin-2-one derivative has formula IIIA,

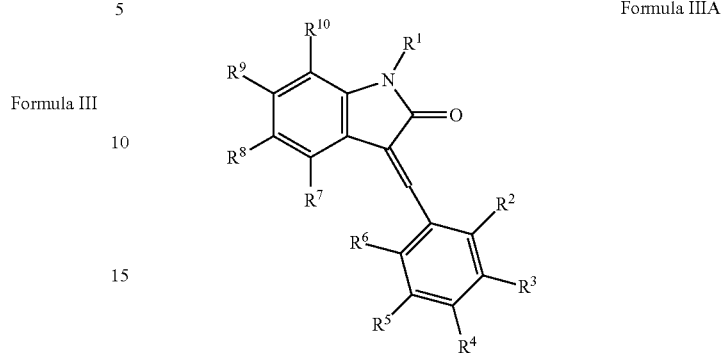

Formula IIIA or salts thereof, wherein $R^1$, $R^2$, $R^3$, $R^4$, $R^5$, $R^6$, $R^7$, $R^8$, $R^9$, and $R^{10}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, and $R^{10}$ are optionally substituted with one or more, the same or different, $R^{11}$;

$R^{11}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is hydrogen.

In certain embodiments, $R^2$ is selected from alkoxy, hydroxy, halogen, and alkyl.

In certain embodiments, $R^4$ is selected from alkoxy, hydroxy, halogen, and alkyl.

In certain embodiments, $R^6$ is selected from alkoxy, hydroxy, halogen, and alkyl.

In certain embodiments, $R^9$ is selected from alkoxy, hydroxy, halogen, and alkyl.

In certain embodiments, $R^2$ is alkoxy.

In certain embodiments, $R^4$ is alkoxy.

In certain embodiments, $R^6$ is alkoxy.

In certain embodiments, $R^9$ is halogen.

In certain embodiments, $R^1$, $R^3$, $R^5$, $R^7$, $R^8$, and $R^{19}$ are hydrogen.

In certain embodiments, the compound of formula III is 3-(3-hydroxy-4-methoxybenzylidene)indolin-2-one;

3-(3,5-dimethoxybenzylidene)-7-fluoroindolin-2-one;

3-([1,1'-biphenyl]-4-ylmethylene)-7-fluoroindolin-2-one;

6-chloro-3-(3,5-dichlorobenzylidene)indolin-2-one or salts thereof.

In certain embodiments, the quinolin-4-amine derivative is a compound of formula IV:

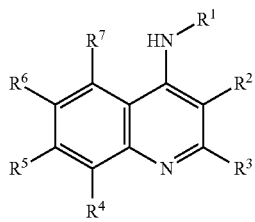

Formula IV or salts thereof wherein, $R^1$ is carbamoyl, phenyl, or phenylcarbamoyl wherein each $R^1$ is optionally substituted with one or more, the same or different, $R^8$;

$R^2$, $R^3$, $R^4$, $R^5$, $R^6$, and $R^7$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^2$, $R^3$, $R^4$, $R^5$, $R^6$, and $R^7$ are optionally substituted with one or more, the same or different, $R^8$;

$R^8$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^9$; and $R^9$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the quinolin-4-amine derivative is 7-chloro-N-(3,5-difluorophenyl)quinolin-4-amine 1-(6-bromoquinolin-4-yl)-3-(4-chlorophenyl)urea or 1-(6-bromoquinolin-4-yl)-3-(2-methyl-3-nitrophenyl)urea or salts thereof.

In certain embodiments, the quinazolin-4-amine derivative is a compound of Formula V:

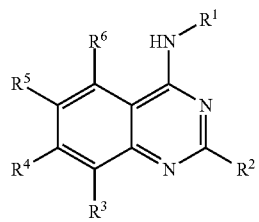

Formula V or salts thereof wherein, $R^1$ is carbocyclyl, aryl, or heterocyclyl wherein each $R^1$ is optionally substituted with one or more, the same or different, $R^7$;

$R^2$ is carbocyclyl, aryl, or heterocyclyl wherein each $R^2$ is optionally substituted with one or more, the same or different, $R^7$;

$R^3$, $R^4$, $R^5$, and $R^6$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^3$, $R^4$, $R^5$, and $R^6$ are optionally substituted with one or more, the same or different, $R^7$;

$R^7$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^8$; and $R^8$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is phenyl or pyrazolyl.

In certain embodiments, the compound is N-(5-methyl-1H-pyrazol-3-yl)-2-phenylquinazolin-4-amine or N-(4-chlorophenyl)-2-phenylquinazolin-4-amine or salts thereof.

Processes of Preparing Compounds

Certain compounds disclosed herein may be prepared using corresponding starting materials as illustrated in the schemes below. In certain embodiments, the disclosure contemplates methods of preparing compounds of formula I comprising mixing an aldehyde or ketone with a compound comprising hydrazine under conditions such that the product is formed. See Mohareb et al., Molecules, 2011, 16, 16-27 and Newkome & Fishel, J. Org. Chem, 1966, 31, 677-681. In one example, compounds are prepared by the following reactions.

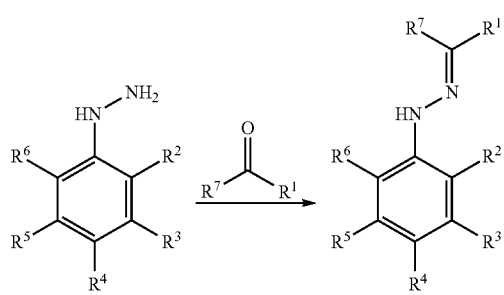

Certain compounds disclosed herein may be prepared using corresponding starting materials as illustrated in the schemes below according to the procedures in Hartung et al., Tetrahedron, 2006, 62, 10055-10064, Luo et al., Tetrahedron Letters, 2002, 43 5739-5742, and Ioannidis et al., J. Med. Chem., 2011, 54, 262-276, or as appropriately modified. All of these are hereby incorporated by reference in their entirety. In certain embodiments, the disclosure contemplates methods of preparing compounds disclosed herein by mixing an aniline compound and a halogenated pyrazole under conditions such that the compounds of formula II are formed.

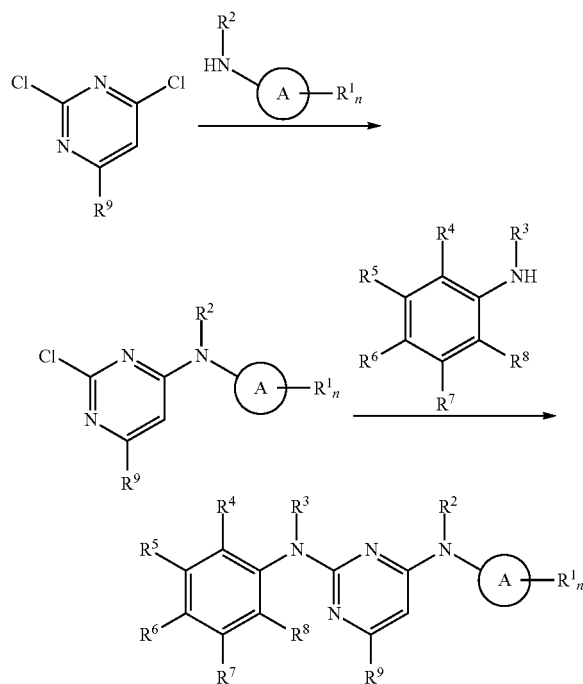

Certain compounds disclosed herein may be prepared using corresponding starting materials as illustrated in the schemes below according to the procedures in Quallich & Morrissey, Synthesis, 1993, 1, 51-53 and Ogawa et al., Chem. Pharm. Bull., 1988, 36, 2253-2258, or as appropriately modified. Both hereby incorporated by reference in their entirety. In certain embodiments, the disclosure contemplates methods of preparing compounds disclosed herein by mixing an aldehyde compound and an oxindole under conditions such that the compounds of formula III are formed.

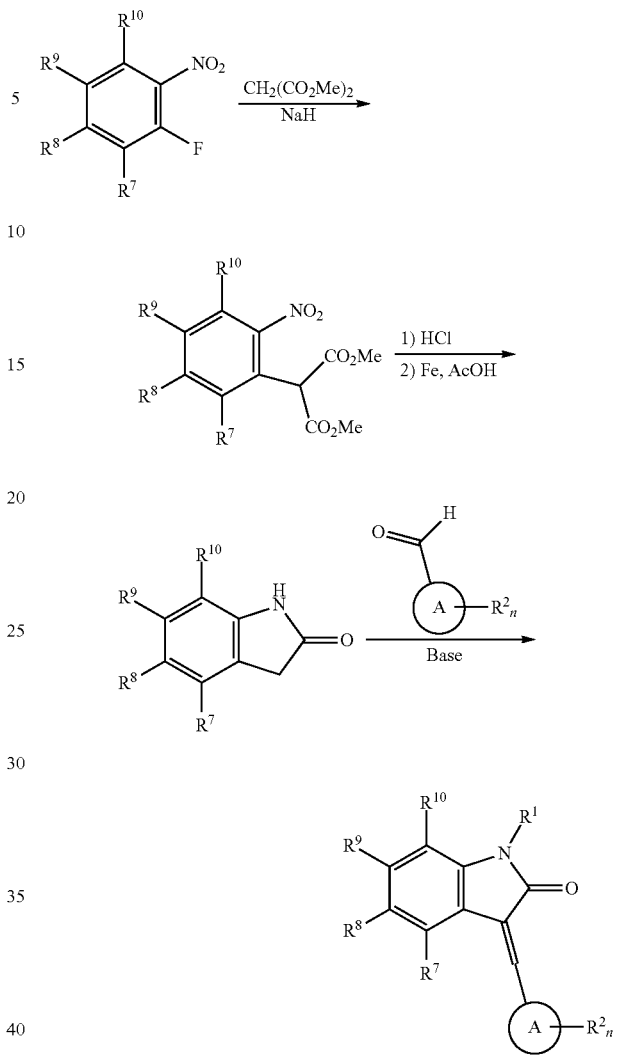

Certain compounds disclosed herein may be prepared using corresponding starting materials as illustrated in the schemes below according to the procedures in Madrid et al. Bioorg. Med. Chem. Lett., 2005, 15, 1015-1018 and Hwang et al., J. Med. Chem., 2011, 54 (20), 7084-7093, or as appropriately modified. Both hereby incorporated by reference in their entirety. In certain embodiments, the disclosure contemplates methods of preparing compounds disclosed herein by mixing a phenol, aniline, or amine compound and a halogenated quinolone under conditions such that the compounds of formula I are formed. Similarly substituted-4-anilinoquinazolines may be prepared as provided in Felts et al., Bioorg Med Chem Lett., 2009, 19(23): 6623-6626 all hereby incorporated by reference in their entirety.

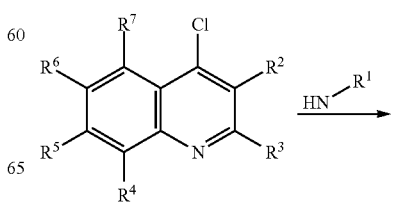

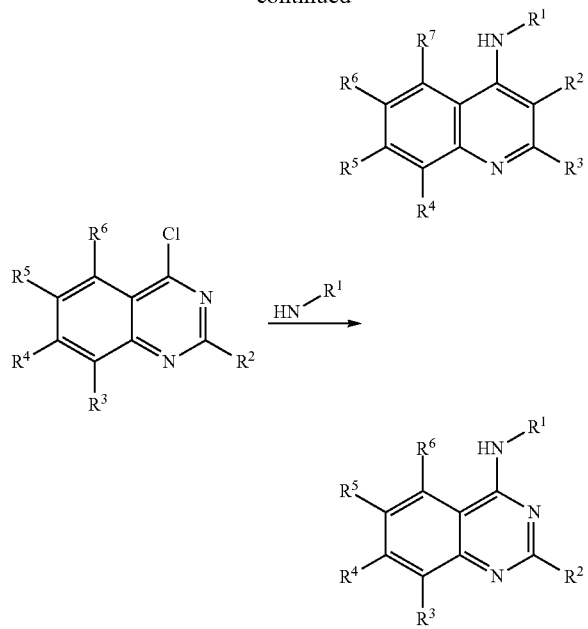

Growth Factors

In some embodiments, the disclosure relates to the combined use of growth factor(s) and compounds disclosed herein and one or more growth factors in cartilage growth applications. Typically, the growth factor is TGF-β1, TGF-β2, TGF-β3, TGF-β4, and/or TGF-β5, CDMP-1, CDMP-2, or combinations thereof. Non-limiting examples of additional suitable growth factors include osteogenin, insulin-like growth factor (IGF)-1, IGF-II, osteoinductive factor (OIF), basic fibroblast growth factor (bFGF), acidic fibroblast growth factor (aFGF), platelet-derived growth factor (PDGF), vascular endothelial growth factor (VEGF), growth hormone (GH), growth and differentiation factors (GDF)-5 through 9, osteogenic protein-1 (OP-1), and bone morphogenetic proteins (BMPs), including but not limited to, BMP-1, BMP-2, BMP-2A, BMP-2B, BMP-3, BMP-3b, BMP-4, BMP-5, BMP-6, BMP-7 (OP-1), BMP-8, BMP-8b, BMP-9, BMP-10, BMP-11, BMP-12, BMP-13, BMP-14, BMP-15. The growth factors may be isolated from synthetic methods, recombinant sources or may be purified from a biological sample. Preferably the growth factors are obtained from a recombinant technology and for clarity certain embodiments include rhBMP-2, rhBMP-4, rhBMP-6, rhBMP-7, and rhGDF-5, as disclosed, for example, in the U.S. Pat. Nos. 4,877,864; 5,013,649; 5,661,007; 5,688,678; 6,177,406; 6,432,919; 6,534,268, and 6,858,431, and in Wozney, J. M., et al. (1988) Science, 242(4885):1528-1534, all hereby incorporated by reference.

Cartilage Matrix

In certain embodiments, the disclosure relates to the regeneration of cartilage through a matrix or scaffold (e.g., hydrogels, sponges, and meshes) comprising compounds disclosed here optionally containing cartilage cells and/or stem cells (e.g., chondrocytes or MSCs) and growth factors. In some embodiments, the disclosure relates to a scaffold or matrix that is a synthetic hydrogel. Poly(ethylene glycol) (PEG) hydrogels are contemplated. Scaffolds, such as PEG hydrogels, may include lactic acid groups, RGD, and decorin moieties. Other contemplated scaffolds include, but are not limited to agarose, alginate, hyaluronic acid (HA), type I and II collagen or other collagen, fibrin, and polyglycolic acid. In certain embodiments, the scaffold alginate may be crosslinked with bivalent cations, commonly calcium, and can support chondrogenesis in a variety of forms (e.g., beads and discs). RGD peptides may be incorporated to provide controllable cell adhesion sites.

In certain embodiments, the scaffold comprises elastin-like polypeptides which include repetitive polypeptides. Certain elastin-like polypeptides comprise the following amino acid sequence [YaaPUaaXaaZaap]n (SEQ ID NO:1) wherein Yaa is alanine or valine; P is proline; Uaa is glycine or alanine; Xaa is glycine, alanine, or valine; Zaa is glycine, alanine, or valine; p is 0, 1, or 2; n is 1 to 1000. In another alternative, the temperature sensitive peptide comprises [VPGG] (SEQ ID NO:2), [VPGVG] (SEQ ID NO:3), [VPAVG] (SEQ ID NO:4), and/or [APGVGV] (SEQ ID NO:5) repeat motifs.

In certain embodiments, the cartilage matrix may be made up of a hydrogel polymer. In one example, the hydrogel is made-up of acrylate polymers and copolymers substituted with an abundance of hydrophilic groups, such as terminal hydroxy or carboxyl groups. In certain embodiments, the graft composition is biodegradable. In certain embodiments, the matrix comprises homopolymers and copolymers consisting of gylcolide and lactide. For certain embodiments, the graft composition comprises a matrix of hydroxyethylmethacrylate or hydroxymethylmethyacrylate polymers. Such a composition may also be made with crosslinkers comprising an ester, anhydride, orthoester, amide, or peptide bond. In some embodiments, crosslinkers contain the following polymers: polyethylene glycol (PEG), polylactic acid, polyglycolide or combinations thereof.

In certain embodiments, the matrix composition may contain one or more antibiotics and/or anti-inflammatory agents. Suitable antibiotics include, without limitation, nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol or any combination thereof.

Suitable anti-inflammatory compounds include both steroidal and non-steroidal structures. Suitable non-limiting examples of steroidal anti-inflammatory compounds are corticosteroids such as hydrocortisone, cortisol, hydroxytriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluocinolone, fluradrenolone acetonide, medrysone, amcinafel, amcinafide, betamethasone and the balance of its esters, chloroprednisone, chloroprednisone acetate, clocortolone, clescinolone, dichlorisone, difluprednate, fluclorinide, flunisolide, fluorometholone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds may also be used.

Non-limiting examples of non-steroidal anti-inflammatory compounds include nabumetone, celecoxib, etodolac, nimesulide, apasone, gold, oxicams, such as piroxicam, isoxicam, meloxicam, tenoxicam, sudoxicam, the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

Cartilage Repair

Cartilage is typically composed of chondroblasts, Type I and Type II collagen fibers, elastin fibers, and proteoglycans. Typical locations within the human body to find cartilage are the joints between bones, the ear, the nose, the elbow, the knee, the ankle, and the intervertebral discs. Cartilage can become damaged because of trauma or disease. In some embodiments, the disclosure relates to using compounds disclosed herein, derivatives, or salts thereof for the repair or regeneration of cartilage such as articular cartilage repair or regeneration or intervertebral disc cartilage repair or regeneration.

Articular cartilage repair is typically done to restore the cartilage on the surface of a bone. Osteochondral autografts or allografts may be performed. In certain embodiments, the disclosure contemplates methods of cartilage repair comprising transplanting sections of cartilage and/or bone to a location where cartilage and/or bone was removed and placing a compound disclosed herein, derivatives, or salts thereof about the surrounding area, e.g., by injections at the site of transplantation. Bone with its cartilage covering may be removed from the same or a different joint and replanted into the hole left from removing degraded bone and cartilage. The transplanted bone and cartilage are typically taken from areas of low stress.

In certain embodiments, this disclosure contemplates removing of articular cartilage e.g. taken from the low weight-bearing area of the patellofemoral joint, and harvesting and expanding the autologous chondrocytes ex vivo followed by re-implantating into areas of the damaged weight-bearing surfaces in combination with administration of a compound disclosed herein. In certain embodiments, the methods further comprise suturing of a collagen membrane, a collagen type I/III membrane, or periosteal flap over the transplanted cells and administering a composition with a compound disclosed herein optionally with chondrocytes, stem cells and growth factors.

In certain embodiments the disclosure related to methods comprising obtaining cartilage from a region of the tissue and mixing it with an enzymatic digestion to release the chondrocytes; expanding the chondrocyte culture to generate sufficient cell numbers for transplantation into a defect within a load-bearing region of the tissue. In certain embodiments, the chondrocyte transplantation is done in combination with a compatible biomaterial comprising a compound disclosed herein to improve chondrocyte retention at the site of transplantation and integration of the graft with the native tissue.

In certain embodiments, the disclosure contemplates compositions comprising chondrocytes and compounds disclosed herein for expanding the chondrocyte culture to generate sufficient cell numbers for transplantation. In certain embodiments, the composition comprises a minimal essential comprising amino acids, salts (e.g., calcium chloride, potassium chloride, magnesium sulfate, sodium chloride, and monosodium phosphate), saccharide (e.g., glucose), and vitamins (e.g., folic acid, nicotinamide, riboflavin, B12) other optional components include phosphates, bicarbonates, iron, and a pH indicator such as phenol red. In certain embodiments, the culture optionally contain blood plasma of a human or other animal, TGFβ1, TGFβ3, platelet-derived growth factor BB (PDGF-BB) and fibroblast growth factor 2 (FGF2), dexamethasone, insulin, RhoA effector kinase, ROCK1 and ROCK2 or inhibitors, e.g., Y27632 and fasudil. In certain embodiments, the components are cultured in a hyperosmolar medium. In certain embodiments, the components are cultured under low oxygen tension.

In certain embodiments, the disclosure contemplated using compounds disclosed herein, derivatives, or salts thereof during chondrocyte implantation. In autologous chondrocyte implantation, cartilage cells are typically extracted arthroscopically from normal articular cartilage of the subject that is located in a nonload-bearing area, e.g., the intercondylar notch or the superior ridge of the femoral condyles, and the cells are replicated, in vitro, in the presence of growth factors. In certain embodiments, the disclosure relates to replicating cartilage cells comprising mixing hyaline cartilage and a compound disclosed herein, derivatives, or salts thereof, under conditions such that the cartilage cells replicate. Typically this is done by adding other growth factors to the cartilage replicating medium, e.g., cartilage-derived morphogenetic proteins (CDMP) and/or TGFβ family proteins. The replicated chondrocytes are implanted to the desired area, e.g., injected about the site of the area for repair optionally in combination with either a membrane or a matrix comprising growth factors such as a CDMP, a TGFβ family protein or a compound disclosed herein.

In certain embodiments, the disclosure contemplated using compounds disclosed herein, derivatives, or salts thereof during marrow stimulating procedures sometimes referred to as microfracture surgery. Damaged cartilage is typically ablated by, e.g., drilling or pounding, exposing the underlying bone—sometimes referred to as a microfracture, to form lesions. The subchondal bone typically generates a blood clot followed by cartilage regeneration. In some embodiments the disclosure relates to methods of generating cartilage by disrupting bone underlying articular cartilage and placing a compound disclosed herein about the area of disruption, e.g., by injecting compounds disclosed herein, derivatives, or salts thereof about the site of disrupted bone for the improved repair or regeneration of cartilage optionally in combination with a growth factor such as a CDMP and/or a TGFβ family protein. Alternatively it is contemplated that the compounds are administered to the subject in a pharmaceutical composition before, during or after the procedure. In another alternative, it is contemplated that a collagen matrix is implanted at the site of the exposed underlying bone to improve chondrogenic differentiation of mesenchymal stem cells. It is also contemplated that the subject may optionally be postoperative injected with compounds disclosed herein, hyaluronic acid, and/or mesenchymal stem cells, e.g., obtained from autologous peripheral blood progenitor cells.

Inflammation of the synovial membrane in a joint causes swelling and joint surface destruction. Removing excess fluid and material by a lavage or debridement frequently resolves arthritic knee inflammation and pain. In certain embodiments, the disclosure relates to the use of compounds disclosed herein, derivatives, or salts thereof before, during, or after a lavage or debridement inside a joint, e.g., arthroscopic lavage, arthroscopic debridement. In arthroscopic debridement, joint material or degenerative cartilage it typically removed by injecting a fluid and removing it with a vacuum.

An intervertebral disc (IVD) is found in between two vertebrae. The IVD contains different tissue types such as the annulus fibrosus (AF), the nucleus pulposus (NP), and end-plates. The AF is made up of mainly collagen type I. The amount of collagen type I decreases and collagen type II increase gradually nearer the NP which is mostly collagen type II dispersed within a proteoglycan-rich gelatinous matrix surrounding the NP.

In certain embodiments, the disclosure contemplates compounds disclosed herein, derivatives, or salts thereof in a silk matrix. Porous silk scaffolds may be used for a variety of tissue-engineering applications, such as the regeneration of bone and cartilage. Removal of sericin from silk reduces immunogenic responses. Silk may form a desired sponge-like structure by freeze-drying a silk solution.

In certain embodiments, it is contemplated that compounds disclosed herein, derivatives, or salts thereof may be used to generate a matrix of annulus fibrosus by mixing with mesenchymal stem cells and growth factors. In certain embodiments, the disclosure contemplates implanting a fabricated intervertebral disc into a subject wherein the disc comprises annulus fibrosus tissue and placing a compound disclosed herein about the site of the implant location, e.g., by injection, optionally in combination with a growth factor such as a cartilage-derived morphogenetic protein (CDMP), e.g., CDMP-1 or CDMP-2, and/or bone morphogenetic proteins, e.g., BMP-2, BMP-5, BMP-7, or BMP-14. The fabricated disc may comprise a NP area with a hydrogel polymer/copolymer matrix or a collagen and/or hyaluronan and/or chondroitin-6-sulfate copolymer. A variety of stem cells, such as mesenchymal stem cells, synovium-derived stem cells (SDSCs), or notochord cells, may be used for rejuvenation of NP cells.

In certain embodiments, the disclosure contemplates mesenchymal stem cell (MSC) cultures comprising compounds disclosed herein, derivatives, or salts thereof to undergo chondrogenic differentiation acquiring a rounded cellular morphology and depositing cartilage-specific extensive extracellular matrix (ECM) molecules such as aggrecan, link protein and collagens type II, type IX and type XI. Typical culture components include DMEM, TGFβ3, dexamethasone and insulin. MSCs derived from synovial tissue typically have enhanced chondrogenic potential and reduced level of hypertrophic differentiation in comparison with MSCs derived from bone marrow.

In certain embodiments, the disclosure relates to compositions comprising compounds disclosed herein and stem cells such as pluripotent stem cells, human embryonic stem cells or induced pluripotent stem cells optionally in combination with chondrocytes, i.e. co-cultures or cultures of the two cell populations separated by a membrane. Cultured cells may be seeded onto hyaluronan-based scaffolds and cultured in standard chondrogenic medium supplemented with a TGF-β such as TGF-3 and an anti-inflammatory agent such as dexamethasone.

Therapeutic Applications

In some embodiments, the disclosure relates to pharmaceutical compositions comprising compounds disclosed herein, derivatives and salts thereof for therapeutic applications. In some embodiments, the disclosure relates to methods of treating chondrodystrophies. Typically an effective amount of a pharmaceutical composition comprising the compound is administered to a subject diagnosed with, at risk of, or exhibiting symptoms of osteoarthritis, achondroplasia, costochondrits, relapsing polychondritis, or articular cartilage damage. The pharmaceutical compositions may provide pain relief or slow down the progression of damage delaying joint replacement (knee replacement) surgery.

In some embodiments, the disclosure relates to using compounds disclosed herein, derivatives, or salts thereof in the treatment of a degenerative intervertebral disc. Typically an effective amount of a pharmaceutical composition comprising the compound is administered to a subject diagnosed with, at risk of, or exhibiting symptoms of a degenerative disc. The compositions may be administered orally or injected directly into an intervertebral disc (IVD), e.g., into the annulus fibrosus (AF) and/or the nucleus pulposus (NP) optionally in combination with a growth factor such as a cartilage-derived morphogenetic protein (CDMP), e.g., CDMP-1 or CDMP-2, or a bone morphogenetic protein, e.g., BMP-5, BMP-7, or BMP-14.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When the compounds of the disclosure contain a hydrogen-donating heteroatom (e.g. NH), the disclsoure also covers salts and/or isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug may include a covalently bonded carrier which releases the active parent drug when administered to a mammalian subject. Prodrugs may be prepared by modifying functional groups present in the compounds in such a way that the modifications are cleaved, either in routine manipulation or in vivo, to the parent compounds. Prodrugs include, for example, compounds wherein a hydroxy group is bonded to any group that, when administered to a mammalian subject, cleaves to form a free hydroxy group. Examples of prodrugs include, but are not limited to, acetate, formate and benzoate derivatives of alcohol functional groups in the compounds. Methods of structuring a compound as prodrugs may be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxy group. It is well known that ester prodrugs are readily degraded in the body to release the corresponding alcohol. See e.g., Imai, Drug Metab Pharmacokinet. (2006) 21(3): 173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds may be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the compound may be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation may be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions may be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the invention as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition.

In this respect, and as stated above, it may be desirable to provide compositions of the invention in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein or compound delivery systems. Proteins and/or compounds may be entrapped in the poly (lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One may attach poly(ethylene glycol) to proteins (PEGylation) to increase the in vivo half-life of circulating therapeutic proteins and decrease the chance of an immune response.

EXPERIMENTAL

C2C12 Cell-Based Screening Assay for TGF-β Activity

The C2C12 cells, a mouse myoblast cell line, were obtained from the American Type Culture Collection (ATCC, Manassas, 8 VA). Cells were grown in Dulbecco's modified Eagle medium (DMEM, Gibco Life Technologies, Rockville, Md.) with 10% non heat inactivated fetal bovine serum (Atlanta Biologicals, Norcross, Ga.). The C2C12 cells at passages 4 to 7 were subcultured in T-75 cm2 flasks at 37° C. in a humidified atmosphere containing 5% $CO_2$. When the flasks reached 80% confluence, the cells were trypsinized and seeded in triplicate at 50,000 cells/well in a 12-well plate for the Dual-Luciferase reporter assay.

The C2C12 cells were seeded at a 50,000 cell/well in 12-well plates on day 1. On day 2, after 24 hr growth, the cells were cotransfected with luciferase reporter construct plasmids, 3TP-Lux (3TP-Lux plasmid that encodes 3 tandem copies of TPA-response element plus the TGF-β-responsive region of the PAI-1 gene cloned in front of a luciferase gene) and pGL4.74 Renilla luciferase control vector for 24 h.

Figure 2:
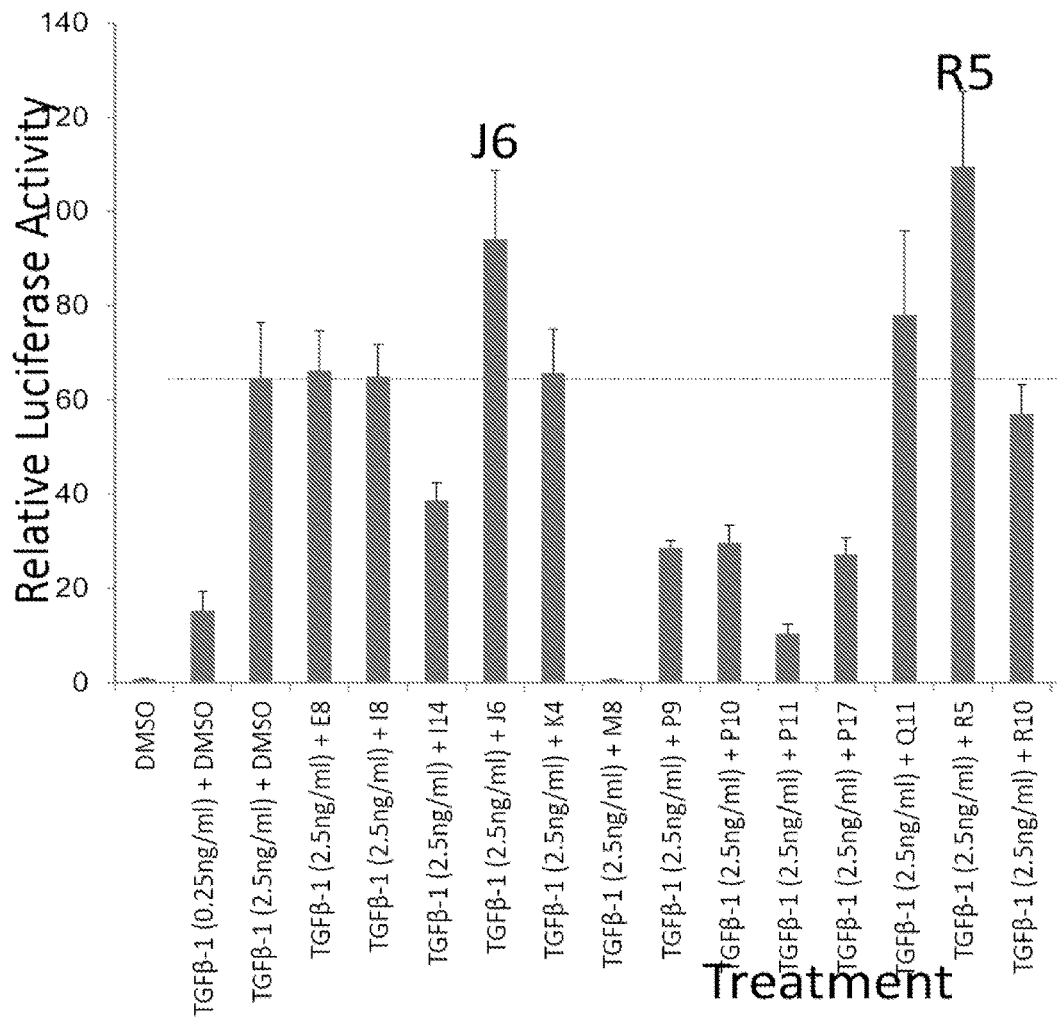
FIG. 2 shows activity data for tested compounds. J6 is 1-(6-bromoquinolin-4-yl)-3-(2-methyl-3-nitrophenyl)urea and $R^5$ is 6-chloro-3-(3,5-dichlorobenzylidene)indolin-2-one.
Figure 3:
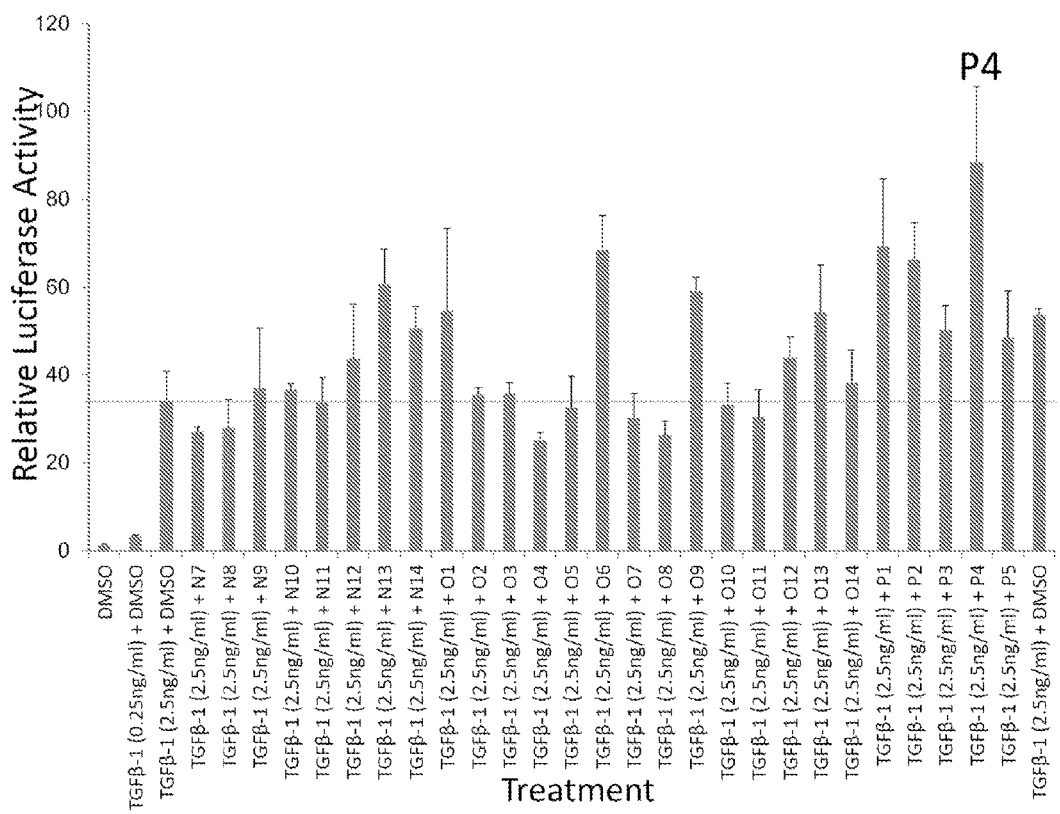
FIG. 3 shows activity data for tested compounds. P4 is $N^2$-(4-chlorophenyl)-$N^4$-(4-fluorophenyl)pyrimidine-2,4-diamine.
Figure 4:
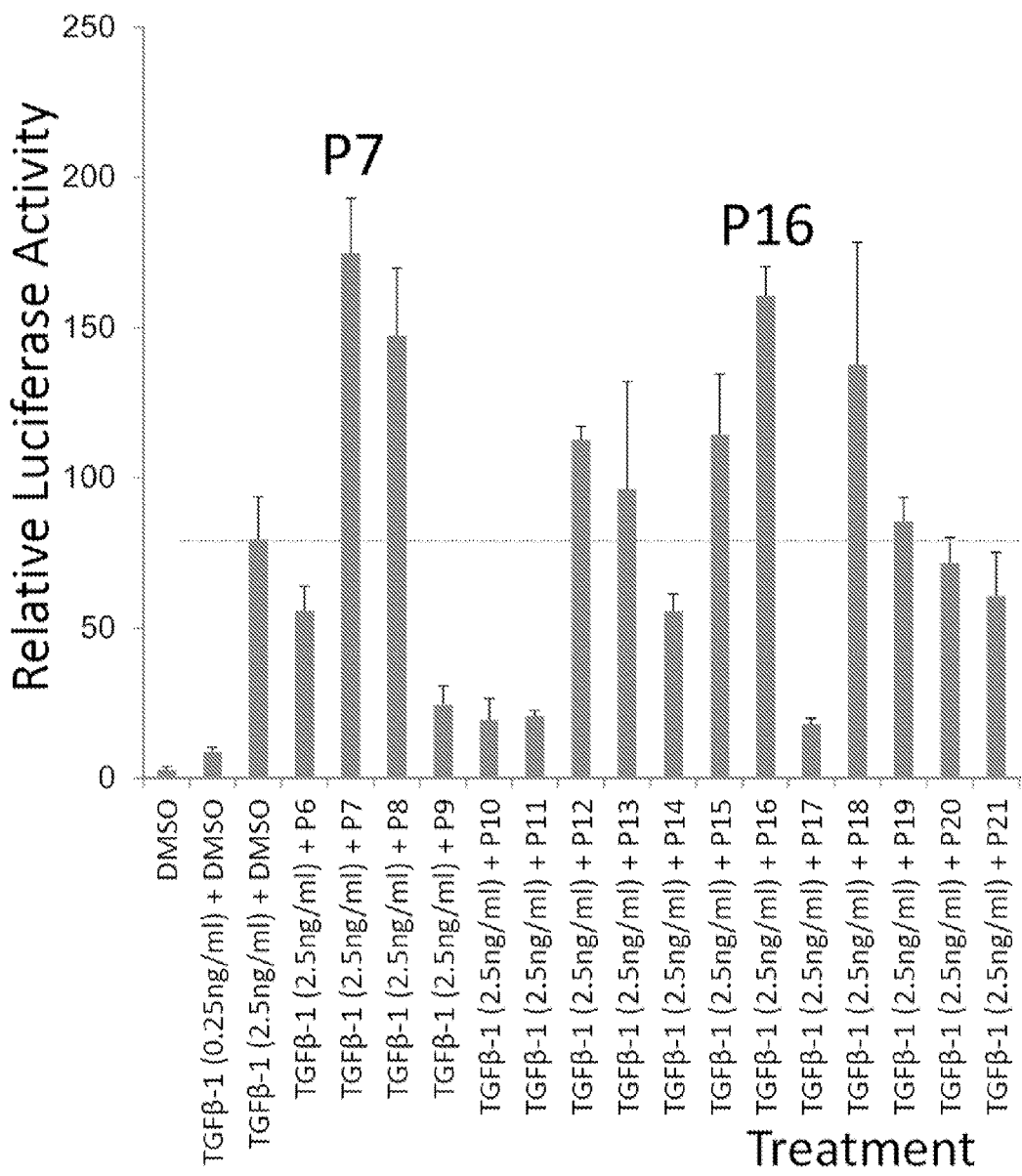
FIG. 4 shows activity data for tested compounds. P7 is $N^2$-(2-fluoro-4-iodophenyl)-$N^4$-(4-fluorophenyl)pyrimidine-2,4-diamine. P16 is $N^2$-(3-chloro-4-methoxyphenyl)-$N^4$-cyclopropylpyrimidine-2,4-diamine.
Figure 5:
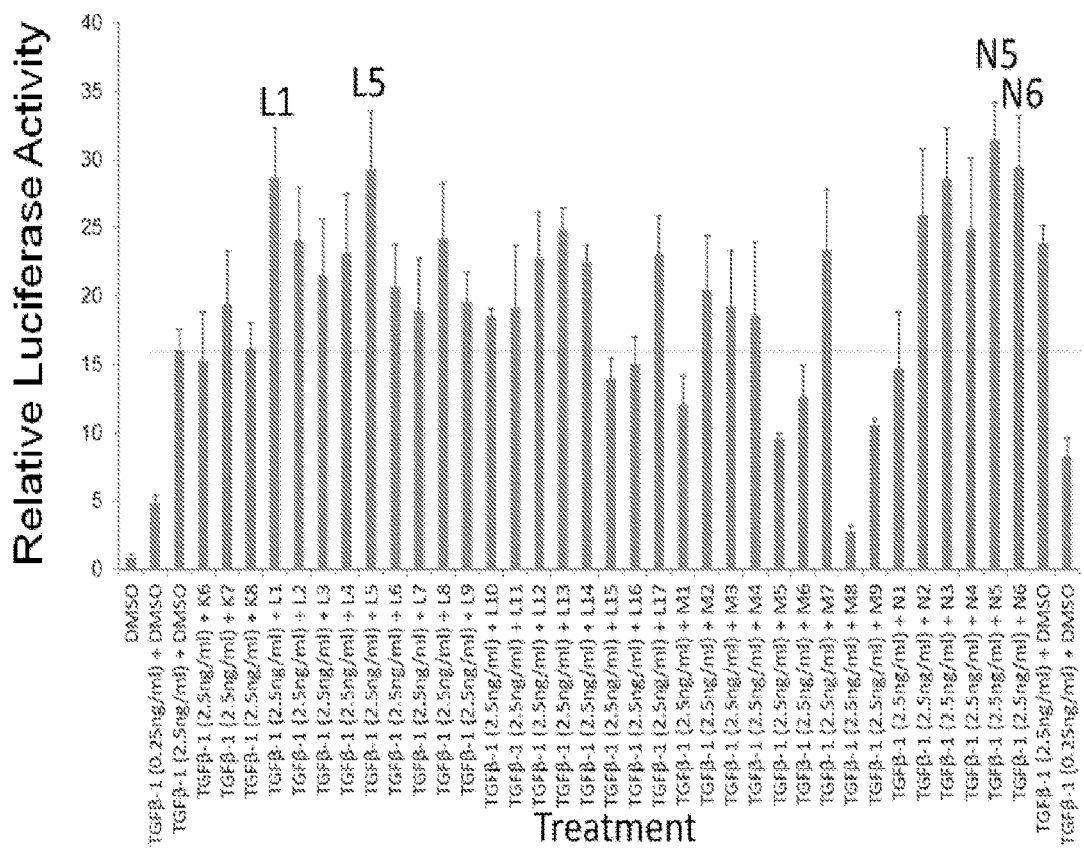
FIG. 5 shows activity data for tested compounds. L1 is 3-(3,5-dimethoxybenzylidene)-7-fluoroindolin-2-one; L53-([1,1'-biphenyl]-4-ylmethylene)-7-fluoroindolin-2-one; N5 is N-(5-methyl-1H-pyrazol-3-yl)-2-phenylquinazolin-4-amine; and N6 is N-(4-chlorophenyl)-2-phenylquinazolin-4-amine
Figure 6:
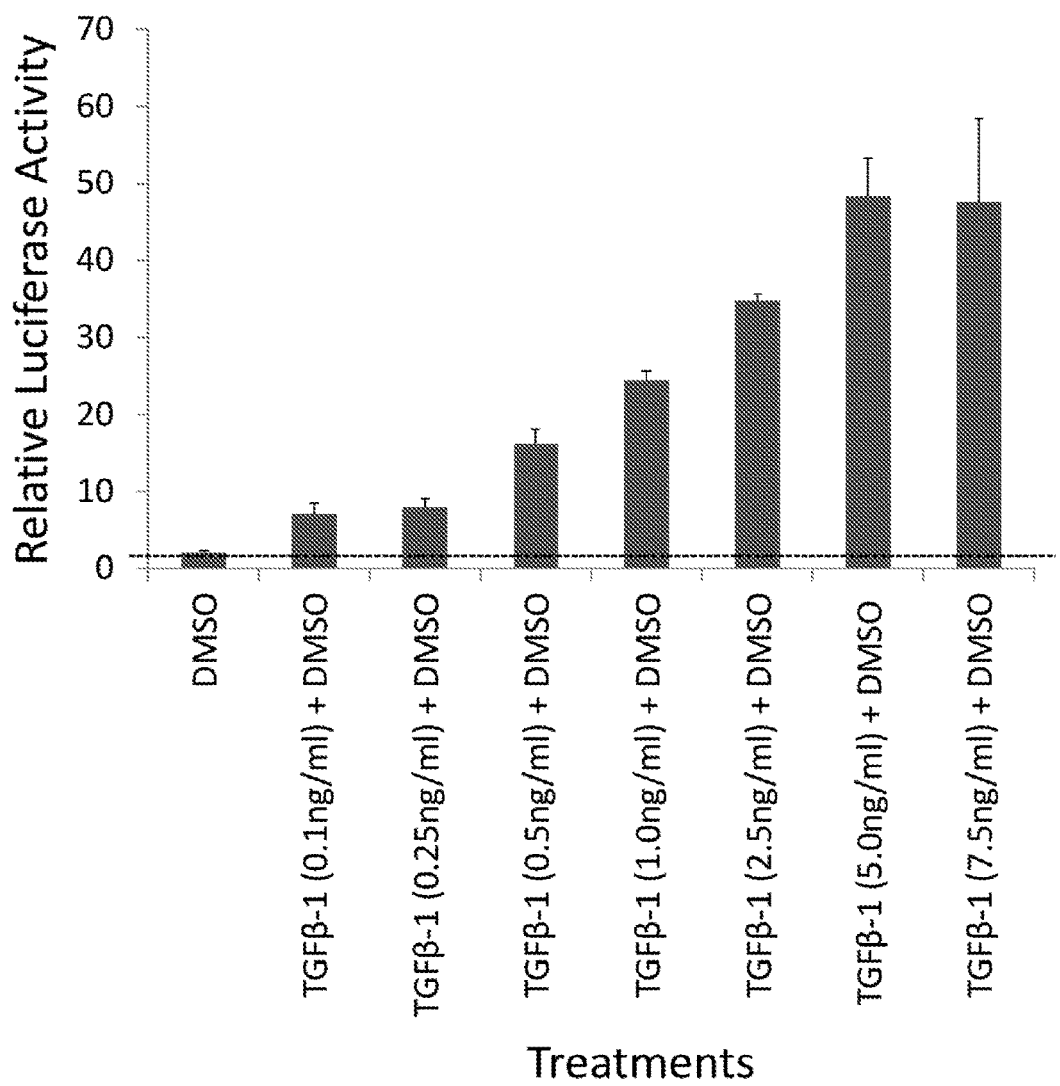
FIG. 6 shows activity data for various doses of TGF-β in the luciferase reporter assay. DMSO solvent is used instead of compounds in this standard assay. Note that maximum response was reached with 5 ng/ml of TGF-β in this optimized screening assay. Doses ranging from 10 ng/ml to 100 ng/ml of TGF-β did not increase reporter response beyond 5 ng/ml dose.

For each well, a total of 1 μg DNA was used for the cotransfection and concentration of pGL4.74 Renilla luciferase vector was 1/15 of 3TP-Lux reporter plasmid. Superfect tranfection reagent (QIAGEN, Valencia, Calif.) was used for the transfection. On day 3, after 24 hr the transfection reagent was removed and the cells were washed with 0% DMEM. The cells were then treated with or without compound for 24 hr. On day 4, the cells were treated with TGF-β1 for 24 hr. On day 5, the luciferase activity was measured using the luciferase assay kit (Promega, Madison, Wis.) according to the manufacturer's instructions on a luminescence reader (Victor™X Light, PerkinElmer Life and Analytical Sciences, Waltham, Mass.). Data were normalized to Renilla luciferase activity and relative luciferase units were shown as firefly luciferase activity/Renilla luciferase activity. Screening results for certain compounds tested are provided in FIGS. 1-5.

What is claimed is:

1. A pharmaceutical composition comprising a compound or salt thereof and a pharmaceutically acceptable excipient, wherein the compound is selected from:
   1-((6-chlorobenzo[d][1,3]dioxol-5-yl)methylene)-2-(3-chlorophenyl)hydrazine;
   3-((2-(3-chlorophenyl)hydrazono)methyl)benzonitrile;
   5-((2-(3-chlorophenyl)hydrazono)methyl)-2-methoxyphenol;
   1-(2-chloro-6-fluorobenzylidene)-2-(3-chlorophenyl)hydrazine;
   1-(3-chlorophenyl)-2-(3-methylbenzylidene)hydrazine;
   methyl 4-((2-(3-chlorophenyl)hydrazono)methyl)benzoate; and
   1-(3-chlorophenyl)-2-(2,4,6-trimethoxybenzylidene)hydrazine.

2. A method of treating damaged cartilage from physical injury or chondrodystrophies comprising administering composition comprising an effective amount of a compound to a human subject in need thereof, wherein the compound has the following formula:

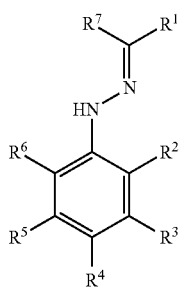

Formula I wherein,
   $R^1$ is phenyl, wherein phenyl is optionally substituted with one, two, or three or more, the same or different, substituents selected from halogen, cyano, hydroxy, methoxy, methyl, methoxycarbonyl, or dioxolyl forming benzo[1,3]dioxolyl with the phenyl;
   $R^3$ is chloro;
   $R^2$, $R^4$, $R^5$, and $R^6$ are each hydrogen; and
   $R^7$ is hydrogen.

3. The method of claim 2, wherein the subject is diagnosed with, exhibiting symptoms of, or at risk of osteoarthritis, achondroplasia, costochondritis, spinal disc herniation, or polychondritis.

4. A method of claim 2 wherein, the composition is administered by injection of a syringe or catheter comprising a lumen for injecting the composition slid through an incision about the area of damaged cartilage.

5. The method of claim 2, wherein the composition is administered by injection in combination with progenitor cells, autologous mesenchymal stem cells, autologous peripheral blood progenitor cells, autologous chondrocytic cells, a TGF-β protein, hyaluronic acid, proteoglycans, growth factors or combinations thereof.

6. A method of treating damaged cartilage from physical injury or chondrodystrophies comprising creating lesions surgically in the cartilage of a human subject extending into subchondral bone and administering a compound to the subject in the area of created lesions, wherein the compound has the following formula:

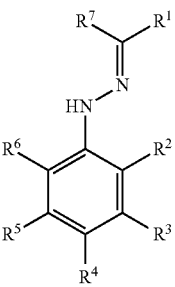

Formula I wherein,
   $R^1$ is phenyl, wherein phenyl is optionally substituted with one, two, or three or more, the same or different, substituents selected from halogen, cyano, hydroxy, methoxy, methyl, methoxycarbonyl, or dioxolyl forming benzo[1,3]dioxolyl with the phenyl;
   $R^3$ is chloro;
   $R^2$, $R^4$, $R^5$, and $R^6$ are each hydrogen; and
   $R^7$ is hydrogen.

7. A method of treating or preventing damaged cartilage from physical injury or chondrodystrophies comprising creating lesions surgically in the cartilage of a human subject extending into subchondral bone and implanting a matrix comprising a compound to the subject in the area of created lesions, wherein the compound has the following formula:

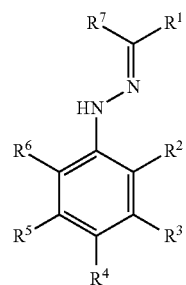

Formula I wherein,
   $R^1$ is phenyl, wherein phenyl is optionally substituted with one, two, or three or more, the same or different, substituents selected from halogen, cyano, hydroxy, methoxy, methyl, methoxycarbonyl, or dioxolyl forming benzo[1,3]dioxolyl with the phenyl;
   $R^3$ is chloro;
   $R^2$, $R^4$, $R^5$, and $R^6$ are each hydrogen; and
   $R^7$ is hydrogen.

8. A method of treating damaged cartilage from physical injury or chondrodystrophies comprising creating lesions surgically in the cartilage of a human subject extending into subchondral bone and implanting a matrix in the area of created lesions, and administering a compound to the subject in the area of created lesions, wherein the compound has the following formula:

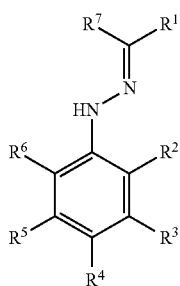

Formula I wherein,
R¹ is phenyl, wherein phenyl is optionally substituted with one, two, or three or more, the same or different, substituents selected from halogen, cyano, hydroxy, methoxy, methyl, methoxycarbonyl, or dioxolyl forming benzo[1,3]dioxolyl with the phenyl;
R³ is chloro;
R², R⁴, R⁵, and R⁶ are each hydrogen; and
R⁷ is hydrogen.

9. The method of claim 7, wherein the matrix comprises collagen.

10. The method of claim 7, wherein the matrix comprises progenitor cells, autologous mesenchymal stem cells, autologous peripheral blood progenitor cells, autologous chondrocytic cells, a TGF-β protein, hyaluronic acid, proteoglycans, growth factors, or combinations thereof.

11. The method of claim 7, further comprising the step of administering progenitor cells, autologous mesenchymal stem cells (MSCs), autologous peripheral blood progenitor cells, autologous chondrocytic cells, a TGF-β protein, hyaluronic acid, proteoglycans, growth factors, or combinations thereof in the area of created lesions.

12. A cartilage matrix comprising a compound or salt thereof,
wherein the cartilage matrix comprises collagen, hydrogel, agarose, alginate, hyaluronic acid (HA), fibrin, or polyglycolic acid, and
wherein the compound has the following formula:

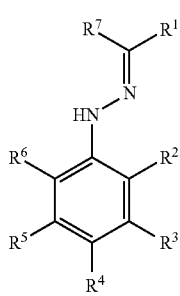

Formula I wherein,
R¹ is phenyl, wherein phenyl is optionally substituted with one, two, or three or more, the same or different, substituents selected from halogen, cyano, hydroxy, methoxy, methyl, methoxycarbonyl, or dioxolyl forming benzo[1,3]dioxolyl with the phenyl;
R³ is chloro;
R², R⁴, R⁵, and R⁶ are each hydrogen; and
R⁷ is hydrogen.

13. The cartilage matrix of claim 12, further comprising progenitor cells, autologous mesenchymal stem cells (MSCs), autologous peripheral blood progenitor cells, autologous chondrocytic cells, a TGF-β protein, hyaluronic acid, proteoglycans, growth factors, or combinations thereof.

14. A kit comprising a cartilage matrix and a compound or salt thereof,
wherein the cartilage matrix comprises collagen, hydrogel, agarose, alginate, hyaluronic acid (HA), fibrin, or polyglycolic acid, and
wherein the compound has the following formula:

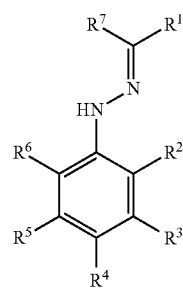

Formula I wherein,
R¹ is phenyl, wherein phenyl is optionally substituted with one, two, or three or more, the same or different, substituents selected from halogen, cyano, hydroxy, methoxy, methyl, methoxycarbonyl, or dioxolyl forming benzo[1,3]dioxolyl with the phenyl;
R³ is chloro;
R², R⁴, R⁵, and R⁶ are each hydrogen; and
R⁷ is hydrogen.

15. The kit of claim 14 further comprising progenitor cells, mesenchymal stem cells (MSCs), peripheral blood progenitor cells, chondrocytic cells, a TGF-β protein, hyaluronic acid, proteoglycans, growth factors, or combinations thereof.

16. A pharmaceutical composition comprising 3-((2-(3-chlorophenyl)hydrazono)methyl)-1H-indole or salt thereof and a pharmaceutically acceptable excipient.

17. A method of treating damaged cartilage from physical injury or chondrodystrophies comprising administering an effective amount of a compound of claim 16, to a subject in need thereof.

18. A cartilage matrix comprising a compound of claim 16 or salt thereof.

19. A kit comprising a cartilage matrix and a compound of claim 16 or salt thereof.

20. The method of claim 17, wherein the subject is a human subject.

21. A cartilage matrix of claim 18, wherein the cartilage matrix comprises collagen, hydrogel, agarose, alginate, hyaluronic acid (HA), fibrin, or polyglycolic acid.

22. The method of claim 2, wherein the compound is selected from:
1-((6-chlorobenzo[d][1,3]dioxol-5-yl)methylene)-2-(3-chlorophenyl)hydrazine;
3-((2-(3-chlorophenyl)hydrazono)methyl)benzonitrile;
5-((2-(3-chlorophenyl)hydrazono)methyl)-2-methoxyphenol;
1-(2-chloro-6-fluorobenzylidene)-2-(3-chlorophenyl)hydrazine;
1-(3-chlorophenyl)-2-(3-methylbenzylidene)hydrazine;

methyl 4-((2-(3-chlorophenyl)hydrazono)methyl)benzoate; and
1-(3-chlorophenyl)-2-(2,4,6-trimethoxybenzylidene)hydrazine.

23. The method of claim 6, wherein the compound is selected from:
1-((6-chlorobenzo[d][1,3]dioxol-5-yl)methylene)-2-(3-chlorophenyl)hydrazine;
3-((2-(3-chlorophenyl)hydrazono)methyl)benzonitrile;
5-((2-(3-chlorophenyl)hydrazono)methyl)-2-methoxyphenol;
1-(2-chloro-6-fluorobenzylidene)-2-(3-chlorophenyl)hydrazine;
1-(3-chlorophenyl)-2-(3-methylbenzylidene)hydrazine;
methyl 4-((2-(3-chlorophenyl)hydrazono)methyl)benzoate; and
1-(3-chlorophenyl)-2-(2,4,6-trimethoxybenzylidene)hydrazine.

24. The method of claim 7, wherein the compound is selected from:
1-((6-chlorobenzo[d][1,3]dioxol-5-yl)methylene)-2-(3-chlorophenyl)hydrazine;
3-((2-(3-chlorophenyl)hydrazono)methyl)benzonitrile;
5-((2-(3-chlorophenyl)hydrazono)methyl)-2-methoxyphenol;
1-(2-chloro-6-fluorobenzylidene)-2-(3-chlorophenyl)hydrazine;
1-(3-chlorophenyl)-2-(3-methylbenzylidene)hydrazine;
methyl 4-((2-(3-chlorophenyl)hydrazono)methyl)benzoate; and
1-(3-chlorophenyl)-2-(2,4,6-trimethoxybenzylidene)hydrazine.

25. The method of claim 8, wherein the compound is selected from:
1-((6-chlorobenzo[d][1,3]dioxol-5-yl)methylene)-2-(3-chlorophenyl)hydrazine;
3-((2-(3-chlorophenyl)hydrazono)methyl)benzonitrile;
5-((2-(3-chlorophenyl)hydrazono)methyl)-2-methoxyphenol;
1-(2-chloro-6-fluorobenzylidene)-2-(3-chlorophenyl)hydrazine;
1-(3-chlorophenyl)-2-(3-methylbenzylidene)hydrazine;
methyl 4-((2-(3-chlorophenyl)hydrazono)methyl)benzoate; and
1-(3-chlorophenyl)-2-(2,4,6-trimethoxybenzylidene)hydrazine.

26. The cartilage matrix of claim 12, wherein the compound is selected from:
1-((6-chlorobenzo[d][1,3]dioxol-5-yl)methylene)-2-(3-chlorophenyl)hydrazine;
3-((2-(3-chlorophenyl)hydrazono)methyl)benzonitrile;
5-((2-(3-chlorophenyl)hydrazono)methyl)-2-methoxyphenol;
1-(2-chloro-6-fluorobenzylidene)-2-(3-chlorophenyl)hydrazine;
1-(3-chlorophenyl)-2-(3-methylbenzylidene)hydrazine;
methyl 4-((2-(3-chlorophenyl)hydrazono)methyl)benzoate; and
1-(3-chlorophenyl)-2-(2,4,6-trimethoxybenzylidene)hydrazine.

27. The kit of claim 14, wherein the compound is selected from:
1-((6-chlorobenzo[d][1,3]dioxol-5-yl)methylene)-2-(3-chlorophenyl)hydrazine;
3-((2-(3-chlorophenyl)hydrazono)methyl)benzonitrile;
5-((2-(3-chlorophenyl)hydrazono)methyl)-2-methoxyphenol;
1-(2-chloro-6-fluorobenzylidene)-2-(3-chlorophenyl)hydrazine;
1-(3-chlorophenyl)-2-(3-methylbenzylidene)hydrazine;
methyl 4-((2-(3-chlorophenyl)hydrazono)methyl)benzoate; and
1-(3-chlorophenyl)-2-(2,4,6-trimethoxybenzylidene)hydrazine.

\* \* \* \* \*

SEQUENCE LISTING

<160> NUMBER OF SEQ ID NOS: 5

<210> SEQ ID NO 1
<211> LENGTH: 13
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: Where YAA is alanine or valine
<220> FEATURE:
<221> NAME/KEY: MISC_FEATURE
<222> LOCATION: (4)..(4)
<223> OTHER INFORMATION: Where P is proline
<220> FEATURE:
<221> NAME/KEY: MISC_FEATURE
<222> LOCATION: (5)..(7)
<223> OTHER INFORMATION: Where GAA is glycine or alanine
<220> FEATURE:
<221> NAME/KEY: MISC_FEATURE
<222> LOCATION: (8)..(10)
<223> OTHER INFORMATION: Where XAA is glycine, alanine, or valine
<220> FEATURE:
<221> NAME/KEY: MISC_FEATURE
<222> LOCATION: (11)..(13)
<223> OTHER INFORMATION: Where ZAA is glycine, alanine, or valine

<400> SEQUENCE: 1

Tyr Ala Ala Pro Gly Ala Ala Xaa Ala Ala Glx Ala Ala
1               5                   10

<210> SEQ ID NO 2
<211> LENGTH: 4
<212> TYPE: PRT
<213> ORGANISM: Homo sapiens

<400> SEQUENCE: 2

Val Pro Gly Gly
1

<210> SEQ ID NO 3
<211> LENGTH: 5
<212> TYPE: PRT
<213> ORGANISM: Homo sapiens

<400> SEQUENCE: 3

Val Pro Gly Val Gly
1               5

<210> SEQ ID NO 4
<211> LENGTH: 5
<212> TYPE: PRT
<213> ORGANISM: Homo sapiens

<400> SEQUENCE: 4

Val Pro Ala Val Gly
1               5

<210> SEQ ID NO 5
<211> LENGTH: 6
<212> TYPE: PRT
<213> ORGANISM: Homo sapiens

<400> SEQUENCE: 5

Ala Pro Gly Val Gly Val
1               5